United States Patent
Harada

[19]

[11] Patent Number: 5,827,231
[45] Date of Patent: Oct. 27, 1998

[54] BLOOD VESSEL DILATOR

[75] Inventor: Kinya Harada, Fujinomiya, Japan

[73] Assignee: Terumo Kabushiki Kaisha, Tokyo, Japan

[21] Appl. No.: 708,748

[22] Filed: Sep. 5, 1996

[30] Foreign Application Priority Data

Sep. 5, 1995 [JP] Japan .................................. 7-254620

[51] Int. Cl.⁶ .................................................. A61M 29/00
[52] U.S. Cl. ............................................ 606/194; 604/96
[58] Field of Search ...................... 606/1, 108, 191–195; 604/96–101

[56] References Cited

U.S. PATENT DOCUMENTS

| | | |
|---|---|---|
| 3,913,565 | 10/1975 | Kawahara . |
| 4,323,071 | 4/1982 | Simpson et al. . |
| 4,782,834 | 11/1988 | Maguire et al. ........................ 606/194 |
| 4,998,917 | 3/1991 | Gaiser et al. ........................... 606/194 |
| 5,176,637 | 1/1993 | Sagae ....................................... 604/96 |
| 5,456,665 | 10/1995 | Postell et al. . |
| 5,507,766 | 4/1996 | Kugo et al. .............................. 606/194 |
| 5,569,200 | 10/1996 | Umeno et al. ........................... 604/96 |
| 5,571,089 | 11/1996 | Crocker ................................... 604/96 |

FOREIGN PATENT DOCUMENTS

0 608 853 A2  8/1994  European Pat. Off. .

*Primary Examiner*—William Lewis
*Attorney, Agent, or Firm*—Burns, Doane, Swecker & Mathis, LLP

[57] ABSTRACT

A blood vessel dilator has an inner tube defining a first passageway therein, an outer tube over the inner tube and forming a second passageway, and a dilating member communicating with the second passageway. The outer tube is constituted by an inner tubular component having a high rigidity, and an outer tubular component covering the inner tubular component. The forward end portion of the outer tubular component protrudes from the distal end of the inner tubular component, and its distal end portion is diametrically constricted to closely contact the inner tube and extends near the distal end of the inner tube.

22 Claims, 5 Drawing Sheets

BLOOD VESSEL DILATOR

BACKGROUND OF THE INVENTION

1. Field of the Invention

The present invention relates to a dilator for a blood vessel, which is useful, in the medical treatment of a stricture or stenosis portion of a blood vessel, for dilating a constricted or stenosis portion of a blood vessel thereby to remedy a blood flow in the blood vessel to the peripheral side.

2. Description of the Related Art

There has been extensively performed a percutaneous transluminal coronary angioplasty (PTCA) for remedying a blood flow to the peripheral side in the medical treatment of a stenosis portion of blood vessel which may be brought about due to arteriosclerosis, etc. The PTCA is performed by percutaneously introducing a catheter provided with a dilating member at the distal end portion into the stenosis portion of blood vessel and then dilating the stenosis portion by the dilating member, thus remedying the blood flow in the blood vessel to the peripheral side.

There is known, as this kind of catheter provided with a dilating member at the distal end portion, a so-called over-the-wire type catheter as represented by a catheter disclosed in U.S. Pat. No. 4,323,071 wherein a guide wire can be movably introduced into the catheter.

Meanwhile, there is an increasing demand in recent years for the employment of a blood vessel dilator for the treatment of the stenosis portion of a finer blood vessel. Therefore, it is now desired to develop a blood vessel dilator which is capable of being introduced into a finer blood vessel (having a smaller diameter) or a more peripheral portion of blood vessel.

The blood vessel dilator of the over-the-wire type which now is in use comprises in general an inner tube having an opened distal end and defining a first passageway therein and an outer tube coaxially mounted over the inner tube so as to form a second passageway therebetween. The distal end of the outer tube is disposed rearward by a predetermined distance from the distal end of the inner tube. A contractible or foldable dilating member is provided which has a distal end fixed to the inner tube and a proximal end fixed to the outer tube. The interior space of the dilating member communicates with the second passageway near the proximal end of the dilating member. Also provided is a hub attached to the proximal ends of both inner and outer tubes.

With regard to this blood vessel dilator of the over-the-wire type, there is a proposal that the distal end of the outer tube should be fixed to the inner tube so as to more effectively transmit the pushing force or torque given to the proximal end portion of the dilator to the distal end of the inner tube at the occasion of introducing the dilator into a blood vessel. Namely, when the distal end portion of the outer tube is fixed to the inner tube in this manner, the pushing force or torque given separately to each of the outer tube and the inner tube through the proximal ends thereof can be joined together at the distal end portion of the outer tube, so that the transmission of the pushing force to the distal end of the inner tube would be improved.

However, there is a problem in this case that since the pushing force is concentrated at the distal end portion of the outer tube, a kinking may possibly be caused at this distal end portion of the outer tube, in particular at the joint portion between the outer tube and the inner tube. Moreover, there is also a possibility that the pushing force or torque thus joined may be absorbed by the flexible distal end portion of the inner tube.

In the case of a highly advanced blood vessel constriction or a calcification, the dilation of the stenosis portion has been performed in two steps. i.e., the stenosis portion is first dilated with a blood vessel dilator provided with a dilating member of small size (1.0 to 1.5 mm in diameter) in an ordinary manner and then the stenosis portion thus partially dilated is re-dilated with a blood vessel dilator provided with a dilating member of larger size (2.0 to 3.0 mm in diameter). However, since this operation requires the insertion of two kinds of dilating catheters into a blood vessel, it imposes a great burden not only to the patient but also to an operator.

SUMMARY OF THE INVENTION

Accordingly, a first object of the present invention is to provide a blood vessel dilator which enables a pushing force or torque given to the proximal end portion of the dilator to be effectively transmitted to the distal end portion of an inner tube, i.e., the distal end portion of the dilator, whereby making it possible to easily insert the distal end portion of the dilator into a stenosis portion of blood vessel.

A second object of the present invention is to provide a blood vessel dilator which is, by itself, capable of performing a dilation of blood vessel not only in such a degree that has been possible with a conventional blood vessel provided with a dilating member of small size, but also in such a degree that has been possible with a conventional blood vessel dilator provided with a dilating member of larger size.

The aforementioned first object has been achieved according to the present invention by a blood vessel dilator which comprises:

an inner tube having an opened distal end and defining a first passageway therein;

an outer tube coaxially mounted over the inner tube so as to form a second passageway therebetween;

a contractible or foldable dilating member communicating with the second passageway;

a first opening formed at a portion of the inner tube disposed proximally from the opened distal end, and communicating with the first passageway; and a second opening formed at a proximal end of the outer tube and communicating with the second passageway;

wherein the outer tube is composed of a rigid inner tubular component and an outer tubular component covering the inner tubular component, a forward portion of the outer tubular component is extended farther from a distal end of the inner tubular component; a distal end portion of the forward portion of the outer tubular component is diametrically contracted fixing onto an outer peripheral surface of the inner tube and extended near the distal end of the inner tube; a third opening for allowing the second passageway to communicate with an interior of the dilating member is formed at proximal end portion of the forward portion of the outer tubular component; a distal end portion of the dilating member is fixed to a portion of the outer tubular component which is contacted with the inner tube; and a proximal end portion of the dilating member is attached to a portion of the outer tubular component which is located rearward of the third opening.

Preferably, the inner tubular component may be formed of a superelastic alloy tube. It is also preferable that the distal end portion of the inner tubular component is more flexible as compared with other portions of the inner tubular component. The aforementioned second object of the present invention would be achieved by allowing the distal end portion of the inner tube which is covered by the outer tubular component of the outer tube to extend from the distal end portion of the dilating member by a distance of 1 mm to 30 mm.

The aforementioned second object has also been achieved according to the present invention a blood vessel dilator which comprises:

an inner tube having an opened distal end and defining a first passageway therein;

an outer tube mounted over the inner tube so as to form a second passageway;

a contractible or foldable dilating member communicating with the second passageway;

a first opening formed at a portion of the inner tube disposed proximally from the opened distal end, and communicating with the first passageway; and a second opening formed at a proximal end of the outer tube and communicating with the second passageway;

wherein a distal end portion of the inner tube is reinforced more strongly than other portions of the inner tube, thus forming a reinforced distal end portion; the distal end portion of the dilating member is fixed to the reinforced distal end portion; the proximal end portion of the dilating member is fixed to the outer tube; and the reinforced distal end portion is extended from the distal end portion of the dilating member by a distance of 1 mm to 30 mm.

Preferably, the reinforced distal end portion should be extended from the distal end portion of the dilating member by a distance of 10 mm or more. It is also preferable that the reinforced distal end portion is constructed by being covered by a synthetic resin tube. The reinforced distal end portion may be provided with an diametrically enlarged portion at a portion which is located forward of the distal end of the dilating member. The reinforced distal end portion may be constructed such that it is formed by being covered by a synthetic resin tube, and at the same time provided with an X-ray contrast marker at a portion which is located forward of the distal end of the dilating member. In this case, the X-ray contrast marker should preferably be interposed between the inner tube and the synthetic resin tube. The aforementioned diametrically enlarged portion may be formed by the provision of this X-ray contrast marker.

DETAILED DESCRIPTION OF THE PREFERRED EMBODIMENTS

The present invention will be explained further with reference to drawings. Throughout the drawings, the identical or similar elements or portions are denoted by the same reference numerals.

Figure 1:
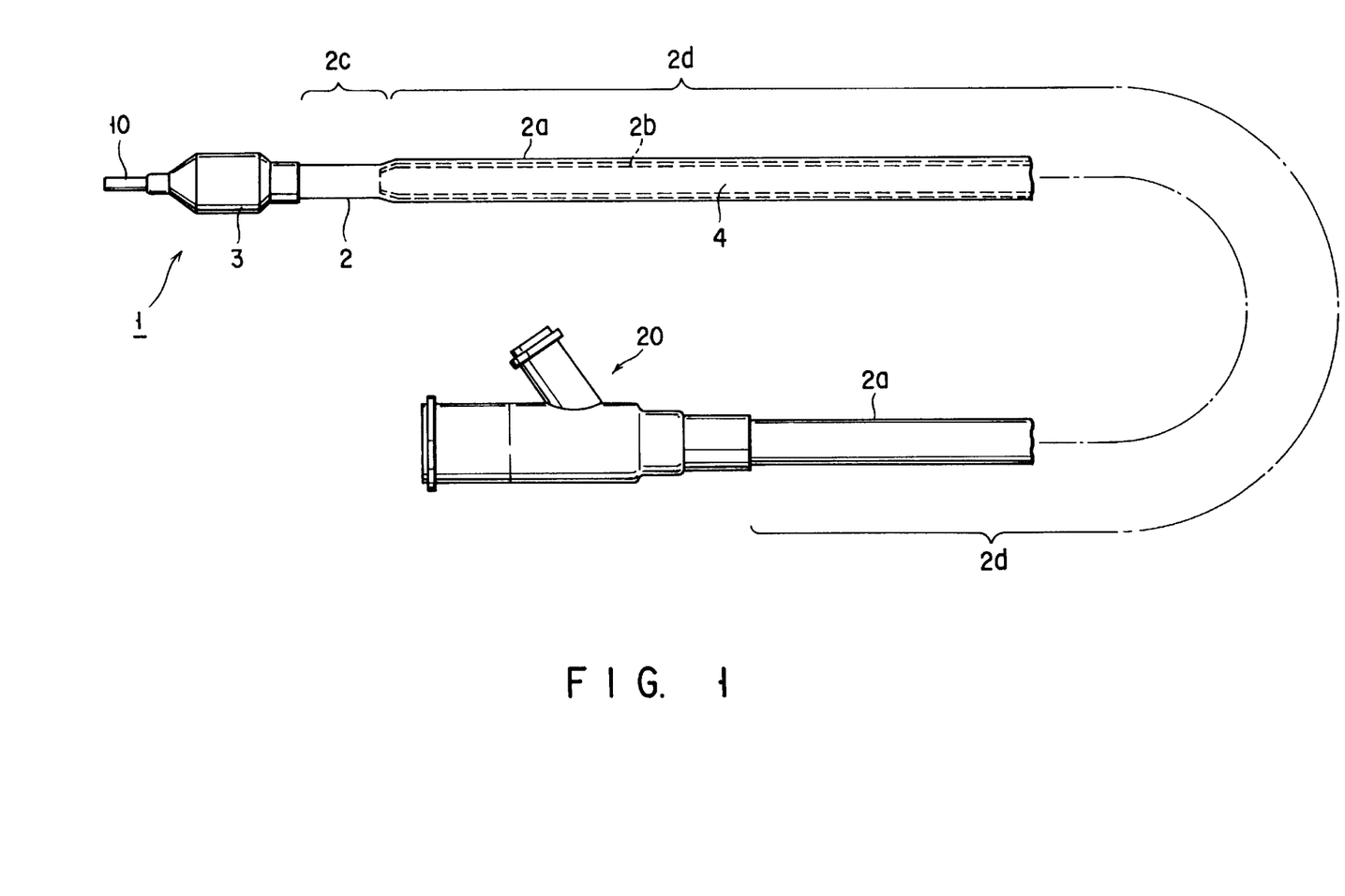
FIG. 1 is a fragmentary plan view of a blood vessel dilator illustrating one embodiment of the present invention.

As shown in FIG. 1, a blood vessel dilator 1 according to the present invention comprises a dilator main body having an inner tube 5 defining a first passageway 4 therein, an outer tube 2 defining a second passageway and a dilating member 3; and a hub 20.

Figure 2:
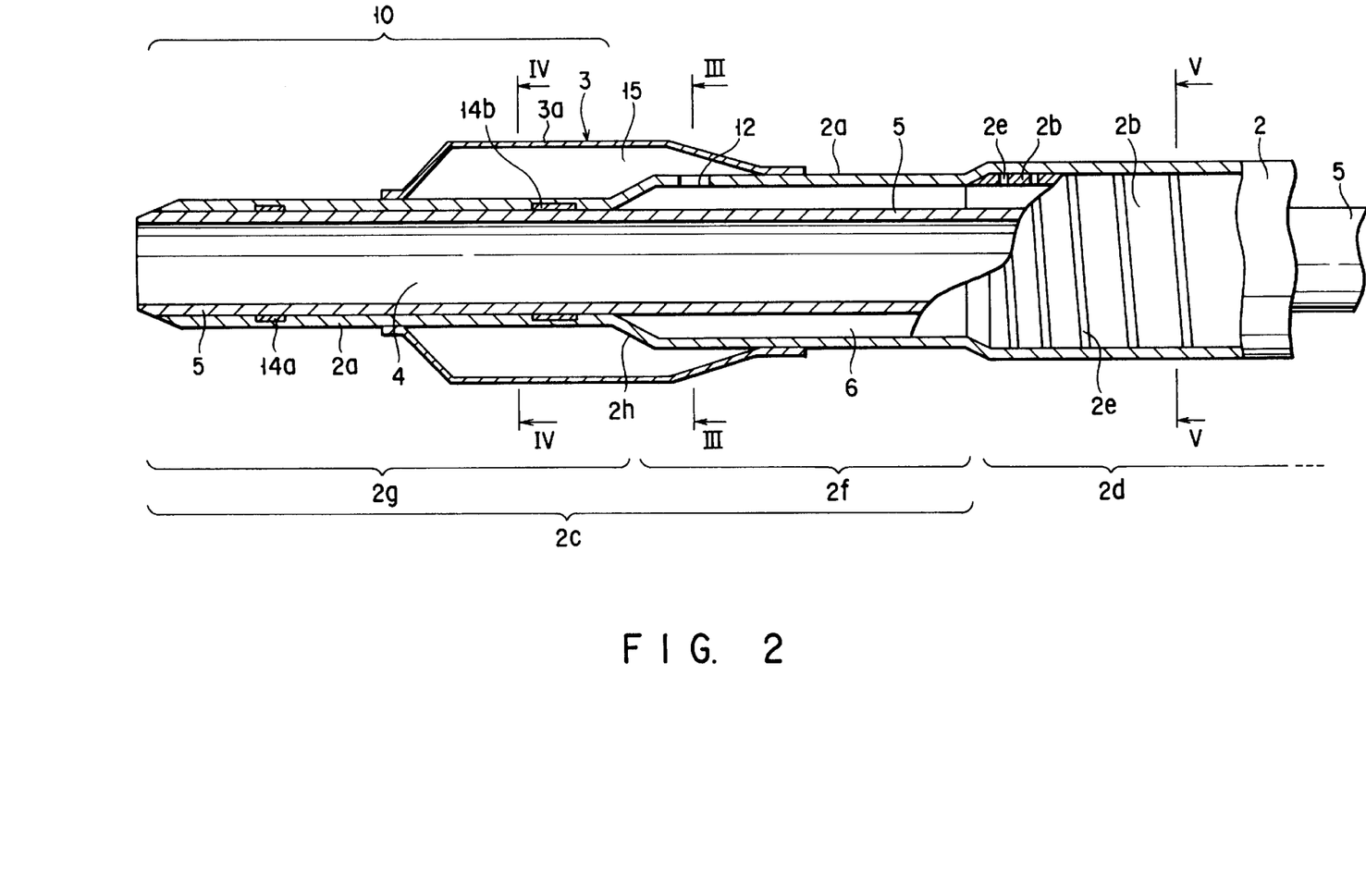
FIG. 2 is an enlarged sectional view illustrating the distal end portion of the blood vessel dilator shown in FIG. 1.

The outer tube 2 is composed of an inner tubular component 2b and an outer tubular component 2a formed of a synthetic resin tube covering the outer peripheral surface of the inner tubular component 2b. The forward portion 2c of the outer tubular component 2a is protruded farther from the distal end portion of the inner tubular component 2b. The forward portion 2c of the outer tubular component 2a consists of three sections as shown in FIG. 2, i.e., a hollow extension 2f which is diametrically contracted more less as compared with the diameter of the proximal portion of the outer tube 2 to have the same inner diameter as that of the inner tubular component 2b, thereby forming an annular space between the inner surface thereof and the outer peripheral surface of the inner tube 5; a tapered portion 2h formed contiguous to the hollow extension 2f and tapered toward the distal end of the outer tubular component 2a; and an inner tube-reinforcing portion 2g extended from the tapered portion 2h and securing onto the outer peripheral surface of the inner tube 5. An opening 12 for allowing the dilating member 3 to communicate with a second passageway 6, hereinafter described, is formed in the distal end portion of the hollow extension 2f or in the tapered portion 2h. The opening 12 may be formed in plurality. The hollow extension 2f may be of the same diameter as that of the proximal portion of the outer tube 2 without being diametrically contracted as mentioned above.

Annular X-ray contrast markers 14a and 14b are interposed between the inner tube-reinforcing portion 2g and the inner tube 5. As shown in FIG. 2, the X-ray contrast marker 14a may preferably be positioned forward of the dilating member 3, whereas the X-ray contrast marker 14b may preferably be positioned at a place which corresponds to an intermediate portion of the dilating member 3. If the X-ray contrast markers are positioned in this manner, the position of the distal end portion 10 of the inner tube-reinforcing portion 2g can be confirmed by the X-ray contrast marker 14a, and at the same time the position of the dilating member 3 can be confirmed by the X-ray contrast marker 14b. Both X-ray contrast markers 14a and 14b may be formed by caulking or adhering a ring formed of a radiopaque material (for example, gold, platinum or an alloy of these materials) onto the outer peripheral surface of the inner tube 5. The X-ray contrast markers 14a and 14b should preferably be interposed between the inner tube-reinforcing portion 2g and the inner tube 5. Because, if the X-ray contrast markers 14a and 14b are disposed in this manner, any stepped portion would not be formed on the outer peripheral surface of the resultant catheter. However, the provision of the X-ray contrast markers is not confined to the aforementioned structure, but may be effected for example by mixing a radiopaque material (for example, tungsten powder, barium sulfate or bismuth subcarbonate) into a raw material for forming the inner tube portion, the outer tubular component or both of these components where the marker is to be put on at the occasion of extrusion-molding these components. The X-ray contrast markers may be formed on the outer peripheral surface of the outer tubular component.

The outer tube 2 may be dimensioned such that the outer diameter thereof is in the range of 0.60 to 2.80 mm, preferably 0.80 to 2.60 mm, the inner diameter thereof is in the range of 0.50 to 2.70 mm, preferably 0.60 to 2.00 mm, the difference between the outer diameter of the inner tube 2 and the inner diameter of the outer tube 2 is in the range of 0.05 to 1.20 mm, preferably 0.1 to 0.60 mm, and the wall thickness thereof is in the range of 0.05 to 0.75 mm, preferably 0.07 to 0.3 mm.

The length of the forward portion 2c (a portion which is not contacted with the inner tubular component 2b) of the outer tubular component 2a may be in the range of 30 to 150 mm, preferably 70 to 120 mm. The length of the hollow extension 2f of the outer tubular component 2a may be in the range of 10 to 100 mm, preferably 30 to 60 mm. The length of the inner tube-reinforcing portion 2g of the outer tubular component 2a may be in the range of 10 to 60 mm, preferably 20 to 50 mm. The distal portion of the forward portion 2c extending from the dilating member 3 may preferably be of a length ranging from 1 to 30 mm. When this distal portion of the forward portion 2c is 1 mm or more in length, the preliminary dilating function of the inner tube-reinforcing portion 2g to a stenosis portion of blood vessel can be effectively exhibited. On the other hand, when this distal portion of the forward portion 2c is 30 mm or less in length, the operability of the dilator on the occasion of introducing the distal end portion thereof into a stenosis portion of blood vessel would be excellently retained. Therefore, the length of the distal portion of the forward portion 2c extending from the dilating member 3 should preferably be in the range of 1 to 30 mm, more preferably 10 to 30 mm, and most preferably 10 to 20 mm.

As shown in FIG. 2, the distal portion of the inner tube 2b is provided with a spiral slit 2e. The provision of this spiral slit is effective in rendering the distal portion of the inner tubular component more flexible. When the distal portion of the inner tubular component 2b becomes flexible in this manner, any difference in physical property between the inner tubular component 2b and the outer tubular component 2a can be minimized, and hence the generation of peeling-off or motional gap between the inner tubular component 2b and the outer tubular component 2a can be prevented and the operability of the dilator can be improved.

The width of the spiral slit 2e to be formed in the inner tubular component 2b may be suitably determined depending on the diameter of the outer tube for instance. However, the width of the spiral slit 2e may generally be in the range of 0.1 mm to 1.5 mm, more preferably 0.5 mm to 1.0 mm. Alternatively, the width of the spiral slit 2e may preferably be in the range of 1/3 to 1/1 of the outer diameter of the inner tubular component. If the width of the spiral slit 2e falls within the aforementioned range, the flexibility of the inner tubular component can be sufficiently assured so that the inner tubular component would not be kinked during the operation of the dilator. The pitch of the slit 2e, if the pitch is assumed to be uniform, may preferably be in the range of 0.3 to 2.0 mm, more preferably 0.5 to 1.0 mm. If the pitch of the spiral slit 2e falls within the aforementioned range, the flexibility of the inner tubular component can be sufficiently assured so that the inner tubular component would not be kinked during the operation of the dilator. The length of the distal end portion of the inner tubular component 2b where the aforementioned slit is to be formed may be suitably determined depending on the entire length of the dilator. However, generally the length of the distal end portion of the inner tubular component 2b where the slit is to be formed may be in the range of 100 to 1,000 mm, more preferably 150 to 500 mm as measured from the distal end of the inner tubular component 2b, the rest of the inner tubular component 2b being not provided with the spiral slit.

Preferably, the spiral slit 2e should be formed such that the pitch of the slit becomes gradually smaller as it approaches the distal end of the inner tubular component 2b, and hence the pitch of the slit becomes gradually larger as it approaches to the proximal end of the inner tubular component 2b as shown in FIG. 2. When the spiral slit 2e is formed such as in a manner as mentioned above, the distal end portion of the inner tubular component 2b becomes increasingly flexible toward the distal end thereof, thus avoiding any abrupt change in physical property, making the bending of the distal portion of the inner tubular component 2b more moderate in shape, and improving the operability of the dilator. If the pitch of the slit is to be gradually altered in this manner, the pitch should preferably be in the range of 0.3 to 3.0 mm at the distal end and in the range of 5 to 10 mm at the proximal end of the slit portion. The pitch of slit at an intermediate portion between the distal end and the proximal end may be an intermediate between the aforementioned ranges, but preferably the pitch of this intermediate portion should also be gradually altered as mentioned above. If the pitch of the spiral slit 2e is formed in this manner, i.e., falling within the aforementioned range, the flexibility of the inner tubular component can be sufficiently assured so that the inner tubular component would not be kinked during the operation of the dilator. Although the slit shown in FIG. 2 is formed of a single spiral line, the slit may be formed of a plurality of spiral lines.

As for the shape of the slit, it may be formed such that the width of the slit is wider at the distal end and narrower at the proximal end. When the spiral slit 2e is formed in this manner, the distal end portion of the inner tubular component 2b becomes increasingly flexible toward the distal end thereof, thus making the bending of the distal portion of the inner tubular component 2b more moderate in shape, and improving the operability of the dilator.

Figure 7:
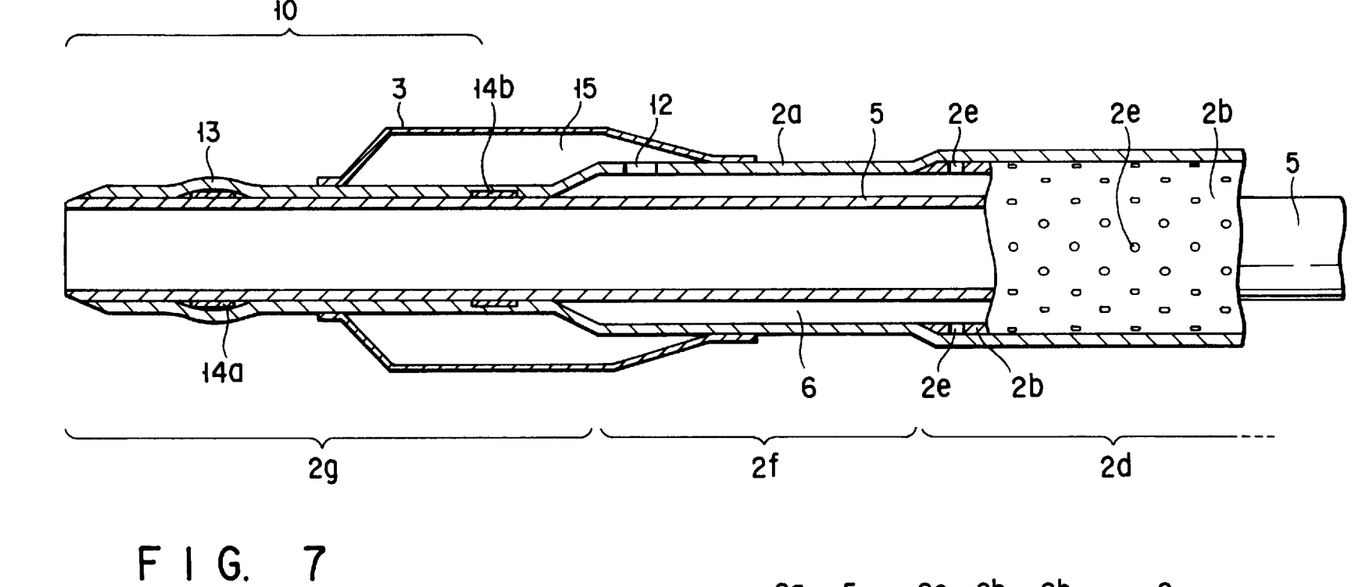
FIG. 7 is a cross-sectional view of the distal end portion of a blood vessel dilator according another embodiment of the present invention.

Alternatively, a large number of fine holes 2e may be formed at the distal end portion of the inner tubular component 2b as shown in FIG. 7 in place of the aforementioned spiral slit 2e. When a large number of fine holes 2e is formed in this manner, the distal end portion of the inner tubular component can be bent more flexibly. When the distal portion of the inner tubular component 2b becomes flexible in this manner, any difference in physical property between the inner tubular component 2b and the outer tubular component 2a can be minimized, and hence the generation of peeling-off or motional gap between the inner tubular component 2b and the outer tubular component 2a can be prevented and the operability of the dilator can be improved.

Since the main portion 2d of the outer tube 2 is provided with an inner tubular component according to this blood vessel dilator 1, the pushing force as well as the torque that have been applied to the proximal end portion of the dilator can be effectively transmitted to the distal end of the inner tube, i.e., an excellent pushability can be achieved. Furthermore, since the distal end portion of the dilator is formed of a synthetic resin, a sufficient flexibility of the distal end portion can be assured. Further, since the distal end portion of the inner tubular component which coincides with the boundary portion between the main portion 2d and the forward portion of the outer tube 2 constitutes a deformable portion which is more flexible than other portions, a kinking of the outer tube 2 at the boundary portion between the highly rigid main portion 2d and the flexible forward portion of the outer tube 2 can be effectively prevented.

As for the materials for forming the inner tubular component 2b, a superelastic alloy; a single metallic substance such as iron, tungsten or copper; an alloy containing any of these metals (for example, an austenitic stainless steel such as SUS 304, SUS 316 or SUS 321; marageing stainless steel; Cu-Zn alloy; or Cu-Sn alloy) may be employed. Among them, a superelastic alloy and an austenitic stainless steel are more preferable.

The superelastic alloy herein referred to is generally known also as a shape-memory alloy and indicates a superelasticity at least at the biological temperature (about 37° C.). Preferable examples of the superelastic alloy include a Ti-Ni alloy containing 49 to 53 atomic % of Ni; a Cu-Zn alloy containing 38.5 to 41.5 wt. % of Zn; a Cu-Zn-X alloy (X=Be, Si, Sn, Al or Ga) containing 1 to 10 wt. % of X; and a Ni-Al alloy containing 36 to 38 atomic % of Al. Among these alloys, the Ti-Ni alloy is more preferable. A portion of the Ti-Ni alloy may be substituted by 0.01 to 10.0 atomic % of X (X=Co, Fe, Mn, Cr, V, Al, Nb, W or B) thereby forming a Ti-Ni-X alloy; or by 0.01 to 30.0 atomic % of X (X=Cu, Pb or Zr) thereby forming a Ti-Ni-X alloy. Further, the mechanical properties of the inner tubular component 2b may be suitably modified by suitably selecting the cold working ratio and/or the conditions for the final heat treatment of the Ti-Ni alloy. Furthermore, the physical properties of the inner tubular component 2b may be suitably modified by suitably selecting the cold working ratio and/or the conditions for the final heat treatment of the Ti-Ni-X alloy.

The inner tubular component 2b may be constructed such that the outer diameter thereof is in the range of 0.6 to 2.0 mm, preferably 0.80 to 1.60 mm, the wall thickness thereof is in the range of 50 to 200 µm, preferably 80 to 150 µm, the length thereof is in the range of 500 to 4,000 mm, preferably 1,000 to 3,000 mm, the buckling strength (the on-load yield stress) thereof is in the range of 5 to 200 kg/mm$^2$ (22° C.), preferably 8 to 150 kg/mm$^2$ (22° C.), and the restoring stress (the off-load yield stress) thereof is in the range of 3 to 180 kg/mm$^2$ (22° C.), preferably 5 to 130 kg/mm$^2$ (22° C.).

The term "super-elasticity" referred to herein should be understood to mean a phenomenon that when an alloy is deformed (bending, stretching or compression) at service temperature to the extent where conventional metals undergo plastic deformation and released from deformation, the alloy resumes the original shapes without need for heating.

The formation of the slits or fine holes in the inner tubular component can be performed by using a laser beam machining (for example, YAG laser), an electric discharge machining, a chemical etching, a cutting work or a combination of these methods.

As for the materials for the outer tubular component 2a of the outer tube 2, a material having some degree of flexibility, such as a thermoplastic resin, e.g. polyolefin (for example, polyethylene, polypropylene, ethylene-propylene copolymer or a cross-linked or partially cross-linked material of them), polyvinyl chloride, ethylene-vinyl acetate copolymer, polyamide elastomer and polyurethane; or silicone rubber may be employed. Among them, the aforementioned thermoplastic resins are preferable for use, polyolefin being most preferable among thermoplastic resin.

The wall thickness of the portion of the outer tubular component 2a that covers the inner tubular component 2b may be 3 to 300 µm, preferably 10 to 200 µm.

A coating of a resin having a bio-compatibility, in particular an anti-thrombogenic property may be coated on the outer tube 2 and on the outer peripheral surface of a dilator (specifically, the outer peripheral surface of the outer tubular component 2a and the dilating member 3). Preferable examples of such a material having an anti-thrombogenic property are polyhydroxyethyl methacrylate and a copolymer of hydroxyethyl methacrylate (HEMA) and styrene (St) (for example, HEMA-St-HEMA block copolymer).

A portion of a resin material constituting the outer tubular component 2a may be protruded into the slit 2e of the inner tubular component 2b. Preferably however, the slit 2e should be substantially free from any protrusion of the resin material constituting the outer tubular component 2a, i.e. the slit 2e should be void, since the deformation of the inner tubular component 2b would not be hindered if the space within the slit 2e is kept free from any protrusion of the resin material.

As for the outer tubular component 2a of the outer tube 2, it may be preferable to employ a heat-shrinkable tube. Namely, it is preferable to employ a heat-shrinkable tube having an inner diameter which is larger than the outer diameter of the inner tubular component 2b so as to allow the inner tubular component 2b to be introduced therein before being heated, and which can be shrunk upon heating so as to allow the heat-shrinkable tube to be closely contacted onto the outer surface of the inner tubular component 2b as well as onto the distal end portion of the inner tube 5. This heat-shrinkable tube can be manufactured by preliminary molding a tube having an inner diameter which is the same as or slightly smaller than the outer diameter of the inner tube, and then by diametrically stretching the resultant tube as a whole, the resultant tube being shrinkable upon heating to a smaller diameter which is the same or almost the same as that formed in the aforementioned molding. As for the material for the heat-shrinkable tube, any material which can be stretched and shrunk upon heating can be used. Examples of such a material are polyolefin (for example, polyethylene, polypropylene or ethylene-propylene copolymer), ethylene-vinyl acetate copolymer and polyamide elastomer.

The inner tube 5 has the first passageway 4, the distal end of which is opened. This first passageway 4 is a passageway for allowing a guide wire to be inserted therein and is communicated with a first opening 9 constituting a guide wire port attached to a hub 20 to be explained hereinafter. The inner tube 5 may be dimensioned such that the outer diameter thereof is in the range of 0.40 to 2.50 mm, preferably 0.55 to 2.40 mm, and the inner diameter thereof is in the range of 0.25 to 2.35 mm, preferably 0.30 to 1.80 mm.

The distal end portion of the inner tube 5 is tapered toward the distal end thereof, whereby facilitating the insertion of the dilator into a blood vessel.

As for the material for the inner tube 5, a material having a some degree of flexibility, such as a thermoplastic resin, e.g. polyolefin (such as polyethylene, polypropylene, ethylene-propylene copolymer), polyvinyl chloride, ethylene-vinyl acetate copolymer, polyurethane and polyamide elastomer; silicone rubber; and latex rubber may be employed. Among them, the aforementioned thermoplastic resins are preferable for use, polyolefin being most preferable among thermoplastic resins.

The distal end portion of the inner tube 5, more specifically a region extending from a portion of the inner tube 5 which corresponds to the intermediate point of the dilating member 3 to the tip end of the inner tube 5 is adhered with the inner tube-reinforcing portion 2g of the outer tubular component 2a thereby forming the reinforced distal portion 10. Since the distal end portion of the inner tube 5 is fixed to the outer tube 2 as described above, the pushing force or torque given separately to each of the outer tube 2 and the inner tube 5 through the proximal end of the dilator can be joined together at the distal end portion of the outer tube 2, so that the transmission of the pushing force to the distal end of the inner tube would be improved. Moreover, since the reinforced distal portion 10 is somewhat rigid, the pushing force given to the proximal end portion of the dilator 1 can be effectively transmitted to the distal end of the dilator 1 thereby facilitating the introduction of the dilator 1 into a stenosis portion of blood vessel. If the length of the reinforced distal portion (a protruded distal portion) 10 extending from the dilating member 3 is 1 mm or more, the preliminary dilation of a stenosis portion of a blood vessel can be realized. Further, if the length of the reinforced distal portion is 10 mm or more, the preliminary dilation of a stenosis portion of blood vessel can be effectively performed, and at the same time, the insertion of the following dilating member into a stenosis portion of a blood vessel can be facilitated. The fixing of the inner tube-reinforcing portion 2g of the outer tubular component onto the inner tube may be performed by making use of an adhesive, but more preferably be performed by making the most of the shrinking force of the outer tubular component made of a heat-shrinkable tube.

The reinforced distal portion 10 may be dimensioned such that the inner diameter thereof is in the range of 0.3 to 0.6 mm, preferably 0.4 to 0.5 mm, and the outer diameter thereof is in the range of 0.5 to 1.1 mm, preferably 0.7 to 0.95 mm.

This reinforced distal portion 10 may be provided with a swelled (diametrically enlarged) portion 13 as shown in FIG. 7. The provision of this swelled portion 13 is advantageous in effectively performing the preliminary dilation of a stenosis portion of blood vessel as well as in facilitating the insertion of the following dilating member into a stenosis portion of blood vessel. A resistance by a stenosis portion of blood vessel to the insertion of the reinforced distal portion 10 may be increased more or less due to the provision of this swelled portion 13. However, since the torque or pushing force given to the proximal portion of the dilator can be effectively transmitted to this reinforced distal portion 10, such an increase in resistance can be disregarded. It is preferable in view of minimizing the aforementioned resistance to make the forward portion of the swelled portion into a gentle tapered or curved shape as shown in FIG. 7. It is also preferable in view of facilitating the withdrawal of the dilator to make the rearward portion of the swelled portion into a gentle tapered or curved shape as shown in FIG. 7. The provision of a swelled portion having such gentle tapered or curved ends can be realized by interposing a ring-like X-ray contrast marker 14a having a semicircular, circular or oval cross-section between the distal end portion of the inner tube 5 and the inner tube-reinforcing portion 2g of the outer tube 2.

Figure 3:
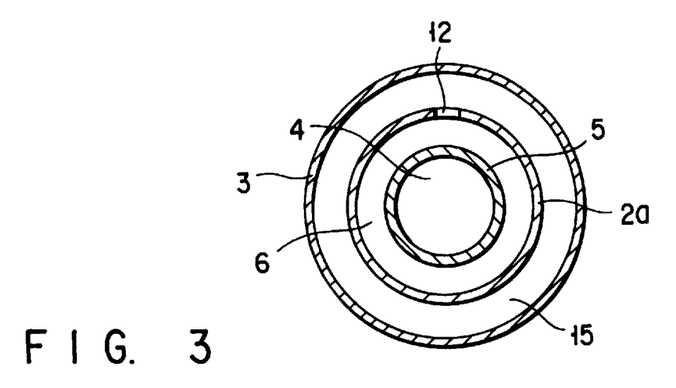
FIG. 3 is a cross-sectional view taken along the line III—III of FIG. 2.
Figure 5:
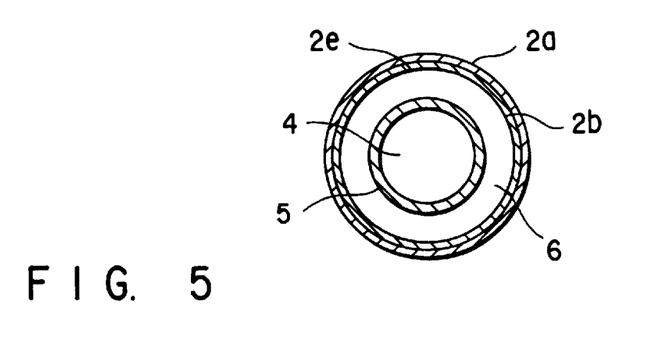
FIG. 5 is a cross-sectional view taken along the line V—V of FIG. 2.

As shown in FIG. 2 or FIG. 5 depicting a cross-sectional view along the line V—V of FIG. 2, the main portion 2d of the outer tube 2 is accompanied with a second passageway 6 formed between the outer peripheral surface of the inner tube 5 and the inner surface of inner tubular component 2b of the outer tube 2. Further, the forward portion 2c (to be exact, the hollow extension 2f) of the outer tubular component 2a is also accompanied with a second passageway 6 formed between the outer peripheral surface of the inner tube 5 and the inner surface of outer tubular component 2a of the outer tube 2 as shown in FIG. 2 or FIG. 3 depicting a cross-sectional view along the line III—III of FIG. 2. The second passageway 6 is annular in cross-section and has a sufficient capacity. This second passageway 6 is communicated via the opening 12 with the internal space of the dilating member 3, and the proximal end of the second passageway 6 is communicated with a second opening 11 of the branched hub 20 constituting an injection port for injecting a fluid (for example, a blood vessel-contrasting medium) for inflating the dilating member 3.

Figure 4:
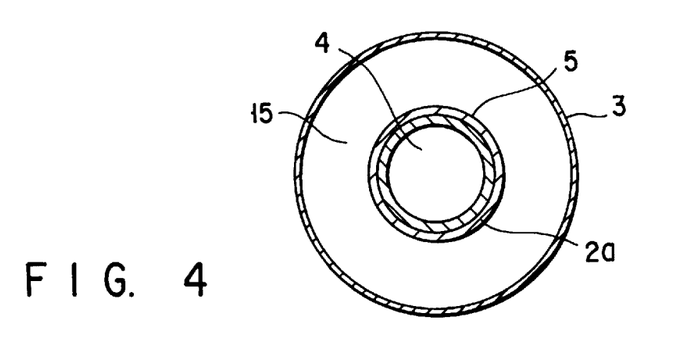
FIG. 4 is a cross-sectional view taken along the line IV—IV of FIG. 2.

The dilating member 3 is contractible or foldable so that when it is not expanded, the dilating member 3 is kept collapsed on the outer peripheral surface of the outer tube 3. The dilating member 3 comprises a cylindrical portion 3a of uniform diameter for effectively dilating a stenosis portion of a blood vessel, this cylindrical portion 3a being also foldable. The shape of this cylindrical portion 3a may not be completely cylindrical but may be polygonal columnar shape. The proximal end portion of the dilating member 3 is fixed by means of an adhesive or a thermal fusion in a liquid-tight manner to a portion of the hollow extension 2f of the outer tubular component 2a which is located rearward of the opening 12. Likewise, the distal end portion of the dilating member 3 is fixed in liquid-tight to a portion of the inner tube-reinforcing portion 2g of the outer tubular component 2b of the outer tube 2. An inflation interior space 15 is formed between the inner surface of the dilating member 3 and the outer surface of the outer tubular component 2a as shown in FIG. 4 depicting a cross-sectional view along the line IV—IV of FIG. 2. This interior space 15 is communicated via the opening 12 with the second passageway 6. Since the rearward portion of the dilating member 3 is communicated with the second passageway 6 having a relatively large capacity, the injection of an inflation medium (fluid) into the dilating member 3 from the second passageway 6 can be easily performed.

As for the material for the dilating member 3, a material having some degree of flexibility, such as a thermoplastic resin, e.g., polyolefin (for example, polyethylene, polypropylene, ethylene-propylene copolymer or a cross-linked or partially cross-linked material of them), polyvinyl chloride, polyvinyl chloride, ethylene-vinyl acetate copolymer, crosslinked type ethylene-vinyl acetate copolymer, polyurethane, polyester such as polyethylene terephthalate, polyamide elastomer; silicone rubber; latex rubber may be employed. Among them, the aforementioned thermoplastic resins are preferable for use.

The forward portion of the dilating member 3 which is located forward of the cylindrical portion 3a as well as the rearward portion of the dilating member 3 which is located rearward of the cylindrical portion 3a are respectively tapered and contacted to the outer tube 2.

The dilating member 3 may be dimensioned, as measured when it is inflated, such that the outer diameter of the cylindrical portion 3a thereof is in the range of 1.50 to 35.00 mm, preferably 2.00 to 30.00 mm, the length of the cylindrical portion thereof is in the range of 10.00 to 80.00 mm, preferably 15.00 to 75.00 mm, and the entire length of the dilating member 3 is in the range of 15.00 to 120.00 mm, preferably 20.00 to 100.00 mm.

A marker 14b formed of a radiopaque material (for example, gold, platinum or an alloy of these materials) is attached to an intermediate portion of the cylindrical portion 3a. When the marker 14b is formed in this manner, the location of the dilating member 3 can be confirmed with the X-ray fluoroscopy. As for the construction of the marker 14b, it may be formed by caulking a ring made of any of the aforementioned metals onto the outer peripheral surface of the inner tube 5. When the marker 14b is attached in this manner, a clear X-ray image can be obtained.

The outer surfaces of the outer tube 2 or dilating member 3, or both of them should preferably be treated so that an excellent lubricity would be exhibited as they are contacted with blood in view of facilitating the insertion of the dilator 1 into a blood vessel or a guide catheter. This surface treatment can be performed by the coating or fixing of a hydrophilic polymer such as poly(2-hydroxyethyl methacrylate), polyhydroxyethyl acrylate, hydroxypropyl cellulose, methylvinyl ether-maleic anhydride copolymer, polyethylene glycol, polyacryl amide and polyvinyl pyrrolidone.

Figure 6:
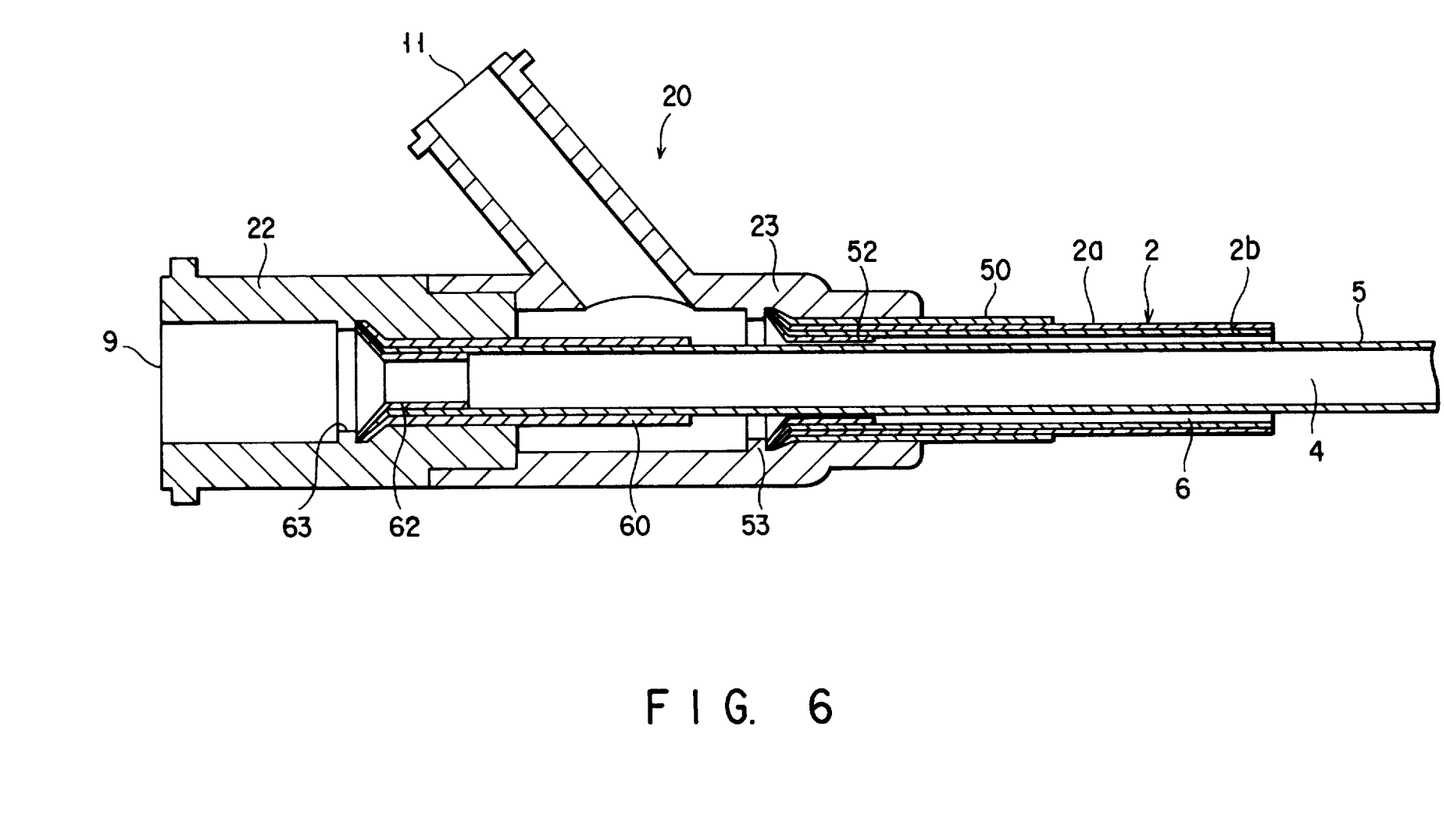
FIG. 6 is a cross-sectional view of the proximal end portion of a blood vessel dilator according one embodiment of the present invention.

As shown in FIGS. 1 and 6, the branched hub 20 comprises an inner tube hub 22 provided with a first opening 9 communicating with the first passageway 4 and constituting a guide wire port, and an outer tube hub 23 provided with a second opening 11 communicating with the second passageway 6 and constituting an injection port, the outer tube hub 23 being attached to the outer tube 2 (a composite consisting of the outer tubular component 2a and the inner tubular component 2b). The outer tube hub 23 and the inner tube hub 22 are fixed to each other.

As for the material for the branched hub 20, a thermoplastic resin such as polycarbonate, polyamide, polysulfone, polyacrylate and methacrylate-butylene-styrene copolymer may be useful.

Specifically, the branched hub 20 is constructed as shown in FIG. 6. Namely, a kink-preventing tube 50 is attached to the proximal end portion of the outer tube 2. This kink-preventing tube 50 is formed of a heat-shrinkable material and can be easily attached to the aforementioned portion by, at first, molding it into a tube having an inner diameter dimensioned such that, upon being thermally shrunk, the inner diameter becomes slightly smaller than the outer diameter of the outer tube 2, and then mounting the tube onto the proximal end portion of the outer tube 2, the resultant tube being subsequently shrunk by heating (for example, by blowing a hot air). On the other hand, the kink-preventing tube 50 is fixed to the outer tube hub 23 by means of a lock pin 52. Namely, the lock pin 52 having a flared end portion and a main tubular component whose outer diameter is approximately equal to the inner diameter of the outer tube 2 is inserted into the rear end portion of the outer tube 2, and then the outer tube 2 is introduced, starting from the distal end portion thereof, into the outer tube hub 23 until the flared end portion of the lock pin 52 passes over an annular rib 53 formed on the inner surface of the outer tube hub 23. Alternatively, the kink-preventing tube 50 may be fixed to the outer tube hub 23 by applying an adhesive to the contacting surfaces of both outer tube hub 23 and kink-preventing tube 50. As for the material for the outer tube hub 23, a thermoplastic resin such as polycarbonate, polyamide, polysulfone, polyacrylate and methacrylate-butylene-styrene copolymer may be useful.

Likewise, a kink-preventing tube 60 is attached to the proximal end portion of the inner tube 5. This kink-preventing tube 60 is formed of a heat-shrinkable material and can be easily attached to the aforementioned portion by first molding it into a tube having an inner diameter dimensioned such that, upon thermally shrunk, the inner diameter becomes slightly smaller than the outer diameter of the inner tube 5, and then mounting the tube onto the proximal end portion of the inner tube 5, the resultant tube being subsequently shrunk by heating (for example, by blowing a hot air). On the other hand, the inner tube 5 attached with the kink-preventing tube 60 is fixed to the inner tube hub 22. Namely, the lock pin 62 having a flared end portion and a main tubular component whose outer diameter is approximately equal to the inner diameter of the inner tube 5 is inserted into the rear end portion of the inner tube 5, and then the inner tube 5 is introduced, starting from the distal end portion thereof, into the inner tube hub 22 until the flared end portion of the lock pin 62 passes over an annular rib 63 formed on the inner surface of the inner tube hub 22. Alternatively, the kink-preventing tube 60 may be fixed to the inner tube hub 22 by applying an adhesive to the contacting surfaces of the inner tube hub 22 and the kink-preventing tube 60. As for the material for the inner tube hub 22, a thermoplastic resin such as polycarbonate, polyamide, polysulfone, polyacrylate and methacrylate-butylene-styrene copolymer may be useful.

As shown in FIG. 6, the outer tube hub 23 and the inner tube hub 22 are fixed to each other. The assembling of these hubs may be performed by introducing the inner tube 5, beginning from the distal end portion thereof, into the outer tube hub 23 via the proximal end portion of the outer tube hub 23, and then by adhering the distal end portion of the inner tube hub 22 onto the proximal end portion of the outer tube hub 23. In this case, the assembling of these hubs may be performed more effectively by coating an adhesive on the contacting surfaces of both outer tube hub 23 and inner tube hub 22.

Instead of attaching the aforementioned branched hub 20 as explained above, a tube having at its rear end portion a port constituting an opening may be hermetically attached to each of the first and second passageways.

The present invention has been described above with reference to an over-the-wire catheter as shown in the FIGUREs, in which the proximal end of the inner tube and the proximal end of the outer tube are positioned at the same position, and the first opening is formed at the proximal end of the dilator main body. However, the present invention should not be limited thereto. A dilator according to the present invention may be of the so-called rapid exchange type, in which the first opening is formed at a position apart from the proximal end of the dilator main body. For example, the inner tube hub 22 is not formed, and instead, a perforation penetrating the inner tubular component and the outer tubular component at a position apart from the proximal end of the dilator main body shown in the FIGUREs. The inner tube is secured by an adhesive or the like around the perforation at its proximal end so that the passageway 4 within the inner tube communicates with the outer atmosphere through the perforation.

Dilation of a stenosis portion of a blood vessel using the dilator shown in FIGS. 1 to 6, or FIG. 7 will be briefly described below.

First, an inflow portion for the blood vessel is insured on a patient body by, for example, the Selzinger method, and a guide wire (not shown) for a guide catheter is retained in the vessel. A guide catheter (not shown) provided with a Y connector at its rear end is inserted in the vessel along the guide wire, retained at the ostium of the coronary artery having a lesion to be treated (stenosis portion), and is removed.

A guide wire (not shown) for a dilator is inserted in the dilator 1 of the invention, and the guide wire-inserted dilator 1 is inserted from the Y connector of the guide catheter into the vessel with the guide wire for a dilator protruding several centimeters from the distal end of the dilator 1. The dilator 1 is advanced in the guide catheter, and enters into the coronary artery having a stenosis portion. Thereafter, the guide wire for a dilator is advanced to the stenosis portion, passed the stenosis portion, and retained.

The dilator 1 of the invention is advanced along the guide wire for a dilator so that the reinforced distal end portion 10 is positioned in the stenosis portion under X-ray perspection with the marker 14b using as a guide. Thus, the stenosis portion is predilated by the reinforced distal end portion 10.

Thereafter, the dilator 1 is further advanced along the guide wire for a dilator until the dilating member 3 is positioned in the pre-dilated stenosis portion under X-ray perspection with the marker 14b using as a guide. Then, from an injector having a pressure gauge, previously connected to the second opening 12 forming an injection port for the dilator 1, a fluid for inflating a dilating member such as blood vessel contrast marker is injected to inflate the dilating member 3, thereby dilating the stenosis portion by pressing.

The blood flow at the peripheral side is confirmed by X-ray contrasting by injecting a contrast medium from a contrast medium injection port (not shown) of the Y connector of the guide catheter. When an improvement in the blood flow is confirmed, the contrast medium is removed through the injection port to deflate or shrink the dilating member 3. Then, after the dilator 1 and the guide wire for a dilator are removed, the guide catheter is removed, and the arrest of hemorrhage is effected by pressing.

As the above guide catheter and the guide wire for a guide catheter, use may be made of those usually used in the PTCA.

Figure 8:
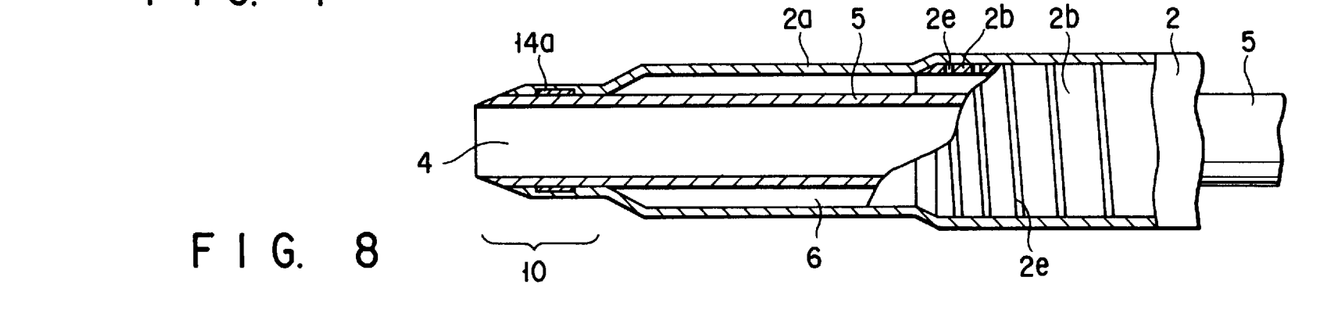
FIG. 8 is a cross-sectional view of the distal end portion of a blood vessel pre-dilator used in pre-dilating a stenosis portion of blood vessel according to the present invention.

In the aforementioned operation, use may be made of a pre-dilating catheter dedicated for pre-dilating a stenosis portion of blood vessel. Such a predilating catheter may have a forward portion 10 with a structure as shown in FIG. 8. The catheter shown has substantially the same structure as described with reference to FIGS. 1 to 6, except that it does not have the dilating member 3, and no branch on the hub 20. In the structure shown in FIG. 8, the reinforced forward portion (pre-dilating portion) 10 has a length of 1 mm to 30 mm, preferably 10 mm to 30 mm for the reasons set forth above. Although the second passageway 6 is formed in FIG. 8, it is not necessarily formed. In pre-dilating a stenosis portion of the blood vessel using the catheter shown in FIG. 8, the catheter is advanced in the blood vessel until the reinforced distal end portion 10 is placed in the stenosis portion in similar manners to those described with reference to the dilator 1. When the pre-dilation is effected by the reinforced distal end portion 10, the catheter and the guide wire are removed from the blood vessel, and exchanged with a conventional catheter provided with a dilating member or a balloon. The re-dilation of the stenosis portion is effected by the conventional catheter in a usual manner. The catheter provided with the balloon may be operated in a conventional manner. For example, a guide wire is inserted into the catheter provided with the balloon, and the guide wire-inserted catheter is instead from the Y connector at the rear end of the guide catheter into the blood vessel with the guide wire protruding several centimeters from the distal end of the catheter. Then, the catheter is advanced in the blood vessel along the guide wire until the balloon is placed in the stenosis portion. The fluid for inflating the balloon is introduced into the balloon to inflate or expand the balloon, thereby dilating the stenosis portion by the inflated balloon.

The present invention will be further explained with reference to the following specific examples.

EXAMPLE 1

A pipe made of Ti-Ni alloy (Ni=51 atomic %) was cold worked to manufacture a super-elastic alloy tube 1.0 mm in outer diameter, 0.85 mm in inner diameter, and about 130 cm in length. A single spiral slit 0.5 mm in width was formed at the forward portion, i.e., 20 cm in distance starting from the distal end of the super elastic alloy tube, the pitch thereof being made gradually larger from 1 mm at the starting point to 10 mm at the terminal point. The slit was formed using a YAG laser beam machine (Miyachi Technos Kabusiki Kaisha, ML-4140A, laser irradiation conditions: 4 W in output and 10 mm/min. in irradiation rate). The slit super-elastic alloy tube thus manufactured was employed as an inner tubular component of the outer tube.

An inner hub and an outer hub as shown in FIG. 6 were prepared from polycarbonate.

On the other hand, by using polyethylene, a tube 0.60 mm in outer diameter and about 1,500 mm in length was prepared, and an inner tube hub was attached to the proximal end portion of the tube thereby to prepare an inner tube.

Further, by using crosslinked polyethylene, a tube 1.05 mm in inner diameter (slightly larger than the outer diameter of the aforementioned super elastic alloy tube) and 0.075 mm in wall thickness was prepared and used as an outer tubular component.

Then, a mandrel having almost the same diameter as the inner diameter of the inner tubular component was inserted into the inner tubular component in such a manner that the forward portion about 10 cm in length of the mandrel was protruded out of the distal end of the inner tubular component. Subsequently, this inner tubular component was inserted into the outer tubular component and heated at a temperature of about 115° C. so as to allow the outer tubular component to shrink, thus closely contacting the outer tubular component onto the outer surfaces of the mandrel and the inner tubular component. Thereafter, the mandrel was withdrawn out of the inner tubular component, and the outer tube hub was attached to the proximal end portion of the outer tubular component, thus manufacturing an outer tube. In this outer tube, any portion of the outer tubular component was not substantially protruded into the slit formed in the inner tubular component, i.e., the slit was void. An opening was formed at a portion of the outer tubular component which was separated forward by 50 mm from the distal end of the inner tubular component.

Meanwhile, an dilating member was formed by making use of crosslinked polyethylene as shown in FIG. 2. Namely, both end portions located forward and rearward of the cylindrical portion of the dilating member were tapered. The cylindrical portion of the dilating member was dimensioned such that when it was inflated, the outer diameter thereof was 2.5 mm and the length thereof was 20 mm. The entire length including the tapered portions of the dilating member was 28 mm.

Then, the inner tube was inserted in the outer tube and fixed to each other. Thereafter, a mandrel was inserted from the distal end of the inner tube so as to introduce a couple of opaque marker (platinum rings), i.e. a first marker and a second marker, from the distal end of the inner tube, the first marker being disposed and fixed at a location which was separated forward by 15 mm from the aforementioned opening, and the second marker being disposed and fixed at a location which was separated forward by 44 mm from the aforementioned opening.

Then, the forward portion about 45 mm in length of the outer tubular component was heated until the forward portion was heat-shrunk, whereby hermetically adhering the forward portion of the outer tubular component onto the forward portion of the inner tube. The length of the portion of the outer tubular component that was extended from the inner tubular component but was not adhered onto the inner tube was 53 mm. Subsequently, the distal end portion of the inner tube was cut off and then tapered by means of heat-working.

Finally, the dilating member was introduced via the distal end of the inner tube over the outer tubular component, and the proximal end portion of the dilating member was adhered using an adhesive onto a portion of the outer tubular component which was located slightly rearward of the aforementioned opening, while the distal end portion of the dilating member was adhered using an adhesive onto a portion of the outer tubular component which was adhered in advance to the inner tube. The length of the inner tube (to be exact, a composite of the inner tube and the outer tube) extending from the distal end of the dilating member was 15 mm.

EXAMPLE 2

The inner tubular component, the outer tubular component, the inner tube, the outer tube and the dilating member employed in this example were the same as those employed in Example 1. Namely, only the assembling method was varied in this example from Example 1.

A mandrel having almost the same diameter as the inner diameter of the inner tubular component was inserted into the inner tubular component. Subsequently, this inner tubular component was inserted into the outer tubular component and heated at a temperature of about 115° C. so as to allow the outer tubular component to shrink, thus closely contacting the outer tubular component onto the outer surfaces of the mandrel and the inner tubular component. Thereafter, the mandrel was withdrawn out of the inner tubular component. In this case, any portion of the outer tubular component was not substantially protruded into the slit formed in the inner tubular component, i.e., the slit was substantially void. An opening was formed at a portion of the outer tubular component which was located 50 mm forward from the distal end of the inner tubular component. Then, a mandrel was introduced into the resultant composite comprising the outer tubular component and the inner tubular component, and the dilating member was inserted over the forward portion of the composite via the distal end thereof. Then, the proximal end portion of the dilating member was adhered by means of thermal fusion onto a portion of the composite which was located slightly rearward of the aforementioned opening. Then, the outer tube hub was attached to the proximal end portion of the composite.

An opaque marker (platinum ring) was attached to two separate locations of the forward portion of the inner tube provided at the proximal end thereof with the inner tube hub, i.e., one location corresponding to the center of the dilating member and the other location being separated forward by a predetermined distance from the distal end of the dilating member. Then, the inner tube was inserted into the outer tube via the proximal end of the outer tube and fixed to each other.

Then, the forward portion about 15 mm in length of the outer tubular component (i.e. from the tip end to a location where the distal end of the dilating member is disposed) was heated to be heat-shrunk, whereby hermetically adhering the outer tubular component onto the forward portion of the inner tube. The distal end portion of the dilating member was adhered onto the outer tubular component by means of heat-fusion. The length of the portion of the outer tubular component that was extended from the inner tubular component but was not adhered onto the inner tube was 80 mm. Subsequently, the distal end portion of the inner tube was cut off and then tapered by means of heat-working.

The length of the inner tube (to be exact, a composite of the inner tube and the outer tube) extending from the distal end of the dilating member was 15 mm.

According to the blood vessel dilator of the present invention, it is possible to effectively transmit the pushing force or torque given to the proximal end portion of the dilator to the distal end of the inner tube constituting the tip end of the dilator, thus allowing the distal end portion of the dilator to be easily introduced into a stenosis portion of blood vessel.

Furthermore, since a reinforced distal end portion protruding 1 mm to 30 mm from the forward end of the dilating member is formed in the blood vessel dilator of the present invention, it is possible, with the employment of this single dilator, to perform not only a preliminary dilation of blood vessel of low expansion degree, but also a sufficient dilation of blood vessel by means of an dilating member without requiring a procedure of exchanging the dilator as in the case of prior art. Moreover, since the dilating member is introduced into a stenosis portion of blood vessel after a preliminary dilation of blood vessel by the reinforced distal end portion, the introduction of the dilating member into a stenosis portion of blood vessel can be facilitated, and at the same time the operability of the dilator would be improved.

What is claimed is:

1. A blood vessel dilator comprising:
   an inner tube having an opened distal end and defining a first passageway therein;
   an outer tube coaxially mounted over the inner tube and defining a second passageway therebetween;
   a contractible or foldable dilating member communicating with the second passageway;
   a first opening formed at a portion of said inner tube disposed proximally from said opened distal end and communicating with said first passageway; and
   a second opening formed at a proximal end of said outer tube and communicating with said second passageway;
   wherein said outer tube is composed of a rigid inner tubular component and an outer tubular component covering said inner tubular component, a forward portion of said outer tubular component being extended farther from a distal end of the inner tubular component; a distal end portion of said forward portion of said outer tubular component is diametrically contracted fixing onto an outer peripheral surface of said inner tube and extended near the distal end of the inner tube; an opening for allowing said second passageway to communicate with an interior of said dilating member is formed at a proximal end portion of said forward portion of said outer tubular component; a distal end portion of said dilating member is fixed to a portion of said outer tubular component which is contacted with said inner tube; and a proximal end portion of said dilating member is attached to a portion of said outer tubular component which is located rearward of said opening.

2. The blood vessel dilator according to claim 1, wherein said inner tubular component is formed of a superelastic alloy tube.

3. The blood vessel dilator according to claim 1, wherein a distal end portion of said inner tubular component is more flexible as compared with other portions of said inner tubular component.

4. The blood vessel dilator according to claim 1, wherein a distal end portion of said inner tubular component which is covered by said outer tubular component is extended from a distal end of said dilating member by a length of 1 mm to 30 mm.

5. A method of dilating a blood vessel comprising introducing a dilator of claim 4 until the distal end portion of the inner tube is placed in a stenosis portion of blood vessel to pre-dilate the stenosis portion by the distal end portion of the inner tube; and forwarding the dilator in the blood vessel until the dilating member is placed in the pre-dilated stenosis portion; and inflating the dilating member, thereby dilating the stenosis portion.

6. A blood vessel dilator comprising:

an inner tube having an opened distal end and defining a first passageway therein;

an outer tube mounted over the inner tube so as to form a second passageway;

a contractible or foldable dilating member communicating with the second passageway;

a first opening formed at a portion of said inner tube disposed proximally from said opened distal end and communicating with said first passageway; and a second opening formed at a proximal end of said outer tube and communicating with said second passageway;

wherein a distal end portion of the inner tube is reinforced more strongly than other portions of the inner tube, thus forming a reinforced distal end portion; the distal end portion of the dilating member is fixed to said reinforced distal end portion; the proximal end portion of the dilating member is fixed to said outer tube; and said reinforced distal end portion is extended from the distal end portion of the dilating member by a distance of 1 mm to 30 mm; and wherein said reinforced distal end portion is provided with a diametrically enlarged portion at a portion which is located forward of the distal end of the dilating member.

7. The blood vessel dilator according to claim 6, wherein said reinforced distal end portion is extended from a distal end of the dilating member by a length of 10 mm or more.

8. The blood vessel dilator according to claim 6, wherein said reinforced distal end portion is constructed by covering a distal end portion of said inner tube with a synthetic resin tube.

9. The blood vessel dilator according to claim 6, wherein said reinforced distal end portion is constructed such that it is formed by being covered by a synthetic resin tube, and provided with an X-ray contrast marker at a portion which is located forward of the distal end of said dilating member.

10. The blood vessel dilator according to claim 9, wherein said X-ray contrast marker is interposed between said inner tube and said synthetic resin tube.

11. A pre-dilator for pre-dilating blood vessel, comprising:

an inner tube defining therein a passageway open at its distal end;

an outer tube mounted over said inner tube; and an opening communicating with said passageway;

wherein the inner tube has a relatively small outer diameter so as to pass through a stenosis portion in a body cavity; the outer tube has an inner diameter and an outer diameter sufficiently larger than an outer diameter of the inner tube, a distal end portion of the outer tube being contracted, brought into close contact with an outer peripheral surface of the inner tube and extending to a vicinity of the distal end portion of the inner tube; the inner and outer diameters of the outer tube, which are formed larger than the outer diameter of the inner tube, are sized so as to transmit a pushing force or torque applied to a proximal end portion of the blood vessel dilator to the distal end portion of the inner tube, thereby enabling pre-dilation of the stenosis portion.

12. The pre-dilator according to claim 11, wherein a portion in which said outer tube is brought into close contact with the outer peripheral surface of said inner tube and has a length of 10 mm or more.

13. The pre-dilator according to claim 11, wherein said reinforced end portion is constituted by the distal end portion of said inner tube covered with a synthetic resin tubular member.

14. The pre-dilator according to claim 11, wherein a portion in which said outer tube is brought into close contact with the outer peripheral surface of said inner tube and is constituted by the distal end portion of said inner tube covered with a synthetic resin tubular member, and the reinforced end portion has a x-ray contrast marker provided therein.

15. The pre-dilator according to claim 14, wherein said marker is provided between said inner tube and said tubular member.

16. The pre-dilator for pre-dilating blood vessel according to claim 11, wherein said outer tube comprises a main part having a highly rigid tubular component and a flexible distal end portion not having the highly rigid tubular component.

17. A method of dilating a blood vessel by using a pre-dilator for pre-dilating blood vessel which comprises an inner tube defining therein a passageway open at its distal end; an outer tube mounted over said inner tube; and an opening communicating with said passageway, wherein a distal end portion of the inner tube has a length of 1 to 30 mm, said method comprising the steps of:

introducing the pre-dilator until the distal end portion of the inner tube is placed in a stenosis portion of blood vessel to pre-dilate the stenosis portion by the distal end portion of said inner tube;

removing the pre-dilator from the blood vessel; and further dilating the pre-dilated stenosis portion using a conventional dilator having a dilating member.

18. A method of dilating a blood vessel by using a dilator comprising an inner tube having an opened distal end and defining a first passageway therein; an outer tube mounted over the inner tube so as to form a second passageway; a contractible or foldable dilating member communicating with the second passageway; a first opening formed at a portion of said inner tube disposed proximally from said opened distal end and communicating with said first passageway; and a second opening formed at a proximal end of said outer tube and communicating with said second passageway; wherein a distal end portion of the inner tube is reinforced more strongly than other portions of the inner tube, thus forming a reinforced distal end portion; the distal end portion of the dilating member is fixed to said reinforced distal end portion; the proximal end portion of the dilating member is fixed to said outer tube; and said reinforced distal end portion is extended from the distal end portion of the dilating member by a distance of 1 mm to 30 mm; said method comprising the steps of:

introducing the dilator until the distal end portion of the inner tube is placed in a stenosis portion of blood vessel to pre-dilate the stenosis portion by the distal end portion of the inner tube; and forwarding the dilator in the blood vessel until the dilating member is placed in the pre-dilated stenosis portion; and inflating the dilating member, thereby dilating the stenosis portion.

19. A blood vessel dilator, comprising:

an inner tube having an opened distal end and defining a first passageway therein;

an outer tube mounted over the inner tube so as to form a second passageway;

a contractible or foldable dilating member communicating with the second passageway;

a first opening formed at a portion of said inner tube disposed proximally from said opened distal end and communicating with said first passageway; and a second opening formed at a proximal end of said outer tube and communicating with said second passageway;

wherein a proximal end portion of the inner tube is introduced through the outer tube to a proximal end portion of the outer tube, the proximal portions of the inner and outer tubes constituting a proximal portion of the blood vessel dilator; a distal portion of the outer tube is diametrically contracted, closely contacts an outer peripheral surface of the inner tube and extends to a vicinity of the distal end of the inner tube; the distal portion of the outer tube has an opening communicating with an interior of the dilating member; a distal end portion of the dilating member is fixed at the portion in which the outer tube contacts the outer peripheral surface; and a proximal portion of the dilating member is fixed onto an outer tube portion which is located rearward of the diametrically contracted portion of the outer tube, thereby resulting in that a pushing force or torque applied to the proximal portion of the blood vessel dilator is given separately to each of the proximal end portions of the inner tube and the outer tube, and separately transmitted through the tubes to the distal end portion of the inner tube at which both tubes are fixed together.

20. The blood vessel dilator according to claim 19, wherein said outer tube comprises a main part having a highly rigid tubular component and a flexible distal end portion not having the highly rigid tubular component.

21. The blood vessel dilator according to claim 20, wherein a distal end portion of the highly rigid tubular component is more flexible than other portions thereof.

22. The blood vessel dilator according to claim 16, wherein a distal end portion of the highly rigid tubular component is more flexible than other portions thereof.

* * * * *

UNITED STATES PATENT AND TRADEMARK OFFICE
CERTIFICATE OF CORRECTION

PATENT NO. : 5,827,231
DATED : October 27, 1998
INVENTOR(S) : Kinya HARADA

It is certified that error appears in the above-identified patent and that said Letters Patent is hereby corrected as shown below:

In Column 10, line 19, delete "liquid tight" and insert -- a liquid-tight manner --.

Signed and Sealed this

Twentieth Day of April, 1999

Attest:

Q. TODD DICKINSON

Attesting Officer        Acting Commissioner of Patents and Trademarks